United States Patent
Lange

(10) Patent No.: US 9,334,221 B2
(45) Date of Patent: May 10, 2016

(54) PRODUCTION OF ACRYLIC ACID

(71) Applicant: SHELL OIL COMPANY, Houston, TX (US)

(72) Inventor: Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/759,462

(22) PCT Filed: Jan. 8, 2014

(86) PCT No.: PCT/EP2014/050184
§ 371 (c)(1),
(2) Date: Jul. 7, 2015

(87) PCT Pub. No.: WO2014/108418
PCT Pub. Date: Jul. 17, 2014

(65) Prior Publication Data
US 2015/0344393 A1 Dec. 3, 2015

(30) Foreign Application Priority Data

Jan. 8, 2013 (EP) .................... 13150519

(51) Int. Cl.
| | | |
|---|---|---|
| C07C 51/00 | (2006.01) | |
| C07C 45/00 | (2006.01) | |
| C07C 29/00 | (2006.01) | |
| C07C 51/16 | (2006.01) | |
| C07C 29/60 | (2006.01) | |
| C07C 45/52 | (2006.01) | |
| C07C 45/65 | (2006.01) | |
| C07C 51/25 | (2006.01) | |

(52) U.S. Cl.
CPC ................ *C07C 51/16* (2013.01); *C07C 29/60* (2013.01); *C07C 45/52* (2013.01); *C07C 45/65* (2013.01); *C07C 51/252* (2013.01)

(58) Field of Classification Search
CPC ........ C07C 29/60; C07C 45/52; C07C 45/65; C07C 51/16
USPC .................................................. 562/532, 599
See application file for complete search history.

(56) References Cited

U.S. PATENT DOCUMENTS 4,138,430 A 2/1979 Stiles et al.

FOREIGN PATENT DOCUMENTS

| WO | 2008089301 | 7/2008 |
| WO | 2010127970 | 11/2010 |
| WO | 2012154450 | 11/2012 |

OTHER PUBLICATIONS

Diaz, Eva. et al.; "Homogeneous Oxidation Reactions of Propanediols at Low Temperatures"; Chem. Sus. Chem.; vol. 3, No. 9; pp. 1063-1070; 2010, XP055062078.
Bettahar, M.M. et al.; "On the partial oxidation of propane and propene on mixed metal oxide catalysts"; Applied Catalysis A: General; vol. 145; pp. 1-48; 1996.
Li, N. et al.; Journal of Catalysis; vol. 270; pp. 48-59; 2010.
Soriano, Dolores, M. et al.; "Tungsten-Vanadium mixed oxides for the oxidehydration of glycerol into acrylic acid"; vol. 13, pp. 2954-2962; 2011.

*Primary Examiner* — Sikarl Witherspoon

(57) ABSTRACT

The invention relates to a process for producing acrylic acid, comprising: converting a C3-oxygenate into acrolein, wherein said C3-oxygenate is selected from the group consisting of 1-propanol, monohydroxyacetone, 2-hydroxypropanal, 3-hydroxypropanal, dihydroxyacetone and 2,3-dihydroxypropanal; and converting the acrolein into acrylic acid. Said C3-oxygenate preferably contains 2 oxygen atoms, and most preferably it is monopropylene glycol.

4 Claims, 1 Drawing Sheet

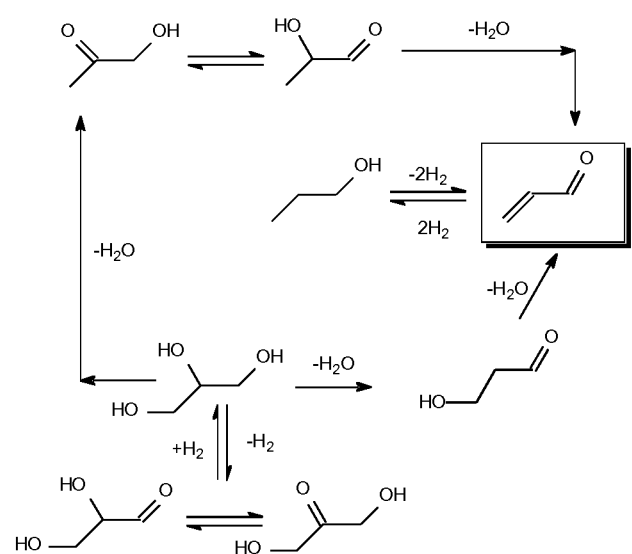

PRODUCTION OF ACRYLIC ACID

PRIORITY CLAIM

The present application is the National Stage (§371) of International Application No. PCT/EP2014/050184, filed Jan. 8, 2014, which claims priority from European Patent No. 13150519.0, filed Jan. 8, 2013 incorporated herein by reference.

FIELD OF THE INVENTION

The present invention relates to a process for producing acrylic acid.

BACKGROUND OF THE INVENTION

Acrylic acid is a chemical for which the worldwide demand is high, about 5 Mt/a (million ton per annum) in 2008 and possibly about 9 Mt/a by 2025. A known route for the production of acrylic acid comprises the oxidation of propene into acrolein (propenal) and then oxidation of the acrolein into acrylic acid. See for example "On the partial oxidation of propane and propene on mixed metal oxide catalysts" by M. M. Bettahar et al. in Applied Catalysis A: General, 145, 1996, p. 1-48. The overall reaction stoichiometry for this route is as follows:

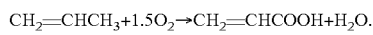

$$CH_2=CHCH_3+1.5O_2 \rightarrow CH_2=CHCOOH+H_2O.$$

A disadvantage of the above-mentioned route for the production of acrylic acid is that two oxygen atoms have to be introduced into the propene by the use of an oxygen containing gas at high temperature (about 350° C.) and with release of a large amount of heat (about 600 kJ/mol). A further disadvantage is that propene has to be used which may be derived from propane. Both propene and propane are currently only readily available as fossil feedstocks and are therefore not renewable.

WO 2012/154450 describes a process in which monopropylene glycol is converted to propanal, which in turn is converted to propenal, which is then oxidized to acrylic acid.

Eva Diaz, et al., Chem. Sus. Chem., 2012, 3(9), 1063 discloses a process for producing acrylic acid comprising preparing acrolein by oxidation of 1,3-propanediol. The acrolein is then oxidized to acrylic acid.

C3-oxygenates contain 3 carbon atoms and 1 or more oxygen atoms. There exist a number of C3-oxygenates which may contain 1, 2 or 3 oxygen atoms and which may be formed as undesired (by)products in certain production processes such as biomass conversion processes. Such biomass conversion process may be the aqueous phase reforming of sugars, as disclosed by N. Li et al. in Journal of Catalysis, 2010, 270, p. 48-59. Examples of such C3-oxygenates are: 1-propanol, monohydroxyacetone, 2-hydroxypropanal, 3-hydroxypropanal, dihydroxyacetone and 2,3-dihydroxypropanal.

Consequently, there is a need in the art to valorize C3-oxygenates in general, which may be formed as undesired (by) products in certain production processes such as biomass conversion processes.

SUMMARY OF THE INVENTION

Surprisingly, it was found that the above-mentioned C3-oxygenates can be valorized by using them in a process for producing acrylic acid, by first converting them into acrolein and then converting the acrolein into acrylic acid. Advantageously, in such way, the C3-oxygenate is converted into a chemical for which the worldwide demand is high, namely acrylic acid. Further, advantageously, in such way, acrylic acid may be produced from a renewable feedstock since the starting C3-oxygenates may originate from biomass conversion processes. Further advantages of the present invention appear from the detailed description below.

Accordingly, the present invention relates to a process for producing acrylic acid, comprising:
converting a C3-oxygenate into acrolein, wherein said C3-oxygenate is selected from the group consisting of 1-propanol, monohydroxyacetone, 2-hydroxypropanal, 3-hydroxypropanal, dihydroxyacetone and 2,3-dihydroxypropanal; and
converting the acrolein into acrylic acid.

BRIEF DESCRIPTION OF THE DRAWINGS

FIG. 1 shows a number of preparation routes starting from C3-oxygenates and resulting in acrolein.

DETAILED DESCRIPTION OF THE INVENTION

In the present invention, a C3-oxygenate is converted into acrylic acid via acrolein as an intermediate.

In the final step of the present process, the acrolein is oxidized into acrylic acid. The present process is illustrated in the following general reaction scheme wherein the starting material for the last step of the process is acrolein:

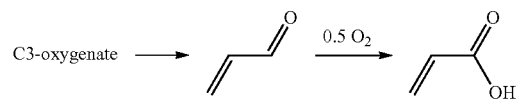

In the present process, the starting material is a C3-oxygenate. Within the present specification, a C3-oxygenate means a compound which contains 3 carbon atoms and 1, 2 or 3 oxygen atoms. The other atoms in such C3-oxygenate are hydrogen atoms. In the present process, the C3-oxygenate is not acrolein, because by C3-oxygenate reference is made herein only to the starting material of the present process.

Further, in the present process, said C3-oxygenate is not glycerol. The conversion of glycerol into acrolein and subsequent conversion of that acrolein into acrylic acid is described in "Tungsten-Vanadium mixed oxides for the oxidehydration of glycerol into acrylic acid" by M. Dolores Soriano et al. in Green Chem., 2011, 13, p. 2954-2962. Said article discloses a one-pot transformation of glycerol into acrylic acid at a modest yield of about 25%, which is not covered by the present invention.

An example of a C3-oxygenate containing 1 oxygen atom which may suitably be used in the present invention is 1-propanol.

Examples of C3-oxygenates containing 2 oxygen atoms which may suitably be used in the present invention are monohydroxyacetone, 2-hydroxypropanal and 3-hydroxypropanal.

Examples of C3-oxygenates containing 3 oxygen atoms which may suitably be used in the present invention are dihydroxyacetone and 2,3-dihydroxypropanal (glyceraldehyde).

Preferably, in the present process, the C3-oxygenate contains 2 oxygen atoms. More preferably, such C3-oxygenate containing 2 oxygen atoms is monohydroxyacetone, 2-hydroxypropanal or 3-hydroxypropanal, even more preferably monohydroxyacetone or 2-hydroxypropanal.

As discussed above, a disadvantage of the route for the production of acrylic acid by oxidation of propene is that two oxygen atoms have to be introduced into the propene by the use of an oxygen containing gas at high temperature (about 350° C.) and with release of a large amount of heat (about 600 kJ/mol). A further disadvantage is that propene has to be used which may be derived from propane, which are both fossil feedstocks and are therefore not renewable.

Surprisingly, with the integrated process of the present invention the above-mentioned disadvantages are avoided, while at the same time, advantageously, by means of the present invention C3-oxygenates, which may be formed as undesired (by)products in certain production processes such as biomass conversion processes, as discussed above, are valorized by transforming them into a chemical for which the worldwide demand is indeed high, namely acrylic acid.

In addition, it has appeared that the present process for the production of acrylic acid has a relatively high route efficiency, also when compared to other acrylic acid production routes using renewable feedstocks, which will now be further explained.

In the present process, acrylic acid is made from a C3-oxygenate which may be obtained from a renewable feedstock. That is, in the present process, acrylic acid is not made from propene that would normally originate from a non-renewable, fossil feedstock. As an alternative, acrylic acid could also be made from propene produced from a renewable feedstock. For example, propene could be produced from a sugar source, which is a renewable feedstock, after which the propene is oxidized into acrylic acid using conventional technologies as already discussed above. The present inventor, however, has found that such an alternative route using a renewable feedstock for providing propene would not be the most efficient route in terms of mass efficiency, carbon efficiency and/or fossil $CO_2$ intensity (or fossil $CO_2$ footprint).

The most efficient route for the production of acrylic acid would be one having effective H/C ratios ($H/C_{eff}$) which is as close to zero as possible for all compounds involved in the production route. $H/C_{eff}$ is defined as follows, based on the carbon content (C), hydrogen content (H) and oxygen content (O) of the compound in question (all expressed as atomic fraction):

$$H/C_{eff} = (H-2*O)/C.$$

For illustration purposes, this definition when applied to $CH_4$ results in $H/C_{eff}=4$. When applied to $CO_2$, it results in the opposite: $H/C_{eff}=-4$. It was surprisingly noticed that both sugars (e.g. glucose) and acrylic acid have $H/C_{eff}=0$. In contrast, propene is characterized by $H/C_{eff}=2$. On the other hand, C3-oxygenates are favourably characterised by a $H/C_{eff}$ which is closer to zero and represent therefore a more efficient feedstock for or intermediate in the production of acrylic acid.

$H/C_{eff}$ values for some C3-oxygenates and the $H/C_{eff}$ values for methane ($CH_4$), carbon dioxide ($CO_2$), sugars (e.g. glucose), acrylic acid and propene are mentioned in the table below.

| Compound | $H/C_{eff}$ |
|---|---|
| methane | 4 |
| propene | 2 |
| 1-propanol | 2 |
| glycerol, monohydroxyacetone, 3- or 2-hydroxypropanal | 0.67 |
| acrolein | 0.67 |
| propanoic acid | 0.67 |
| sugars (e.g. glucose) | 0 |

-continued

| Compound | $H/C_{eff}$ |
|---|---|
| dihydroxyacetone, dihydroxypropanal | 0 |
| 2- or 3-hydroxypropanoic acid | 0 |
| acrylic acid | 0 |
| carbon dioxide | -4 |

$H/C_{eff}$ means effective H/C ratio, as defined above.

This surprising finding can be demonstrated by means of the following calculations for different routes all using glucose as common feedstock and acrylic acid as common product. All individual reactions steps were considered and added to one another to develop the overall reaction equations, assuming 100% molar selectivity. The hydrogen needed for hydrogenation reactions is assumed to come from partial oxidation of methane with the following reaction stoichiometry:

$$CH_4+0.5O_2+H_2O \rightarrow 3H_2+CO_2.$$

Therefore, the use of hydrogen obtained from methane in the above way results in the emission of $CO_2$ the carbon of which $CO_2$ originates from a fossil feedstock (i.e. methane). Such $CO_2$ is herein referred to as "fossil $CO_2$".

Such emission of fossil $CO_2$ could be avoided by producing hydrogen from a renewable feedstock, such as a sugar source (e.g. glucose), with the following overall reaction stoichiometry:

$$C_n(H_2O)_n+nH_2O \rightarrow 2nH_2+nCO_2.$$

However, the gain achieved by the reduction of fossil $CO_2$ emissions would then be more than offset by additional losses in mass efficiency and carbon efficiency which would result in increased feedstock consumption, as illustrated by the above overall reaction stoichiometry.

In the table below, the overall mass efficiency, carbon efficiency and fossil $CO_2$ intensity are mentioned for the acrylic acid production route of the present invention and for a comparative acrylic acid production route wherein the acrylic acid is produced by oxidation of propene which propene is obtained from converting a sugar source. The overall mass efficiency, carbon efficiency and fossil $CO_2$ intensity for each route were calculated as follows:

Overall mass efficiency (wt. %; hereinafter "ME")=
 [(mass of acrylic acid)/(total mass of feed)]*100

Overall carbon efficiency (C %; hereinafter "CE")=
 [(carbon in acrylic acid)/(total carbon in feed)]
 *100

Overall fossil $CO_2$ intensity (C %; hereinafter "FCI")=
 [(carbon from $CH_4$)/(carbon in acrylic acid)]*100

In general, it is preferred to have an overall mass efficiency and overall carbon efficiency which are as high as possible, in combination with an overall fossil $CO_2$ intensity which is as low as possible.

| | $H/C_{eff}$ | ME (wt. %) | CE (C %) | FCI (C %) |
|---|---|---|---|---|
| Route via propene (comparison): step 1: glucose hydrogenolysis → 1- or 2-propanol step 2: 1- or 2-propanol dehydration → propene step 3: propene oxidation → acrylic acid Overall: $C_6H_{12}O_6 + 4O_2 +$ | 2 | 42 | 75 | 33 |

-continued

| | $H/C_{eff}$ | ME (wt. %) | CE (C %) | FCI (C %) |
|---|---|---|---|---|
| $2CH_4 \rightarrow 2C_2H_3COOH + 6H_2O + 2CO_2$ Route via glycerol and acrolein: step 1: glucose cleavage→ 2 × dihydroxypropanal step 2: dihydroxypropanal hydrodeoxygenation → hydroxypropanol + water step 3: hydroxypropanol + water → acrolein + water step 4: acrolein oxidation → acrylic acid Overall: $C_6H_{12}O_6 + 4/3O_2 + 2/3CH_4 \rightarrow 2C_2H_3COOH + 10/3H_2O + 2/3CO_2$ | 0.67 | 62 | 90 | 22 |

$H/C_{eff}$ means effective H/C ratio, as defined above.

The mentioned value for $H/C_{eff}$ is the one for the least favourable compound, i.e. having the highest $H/C_{eff}$, from the whole route in question. All routes both start and end with $H/C_{eff}=0$, for glucose and acrylic acid, respectively.

ME, CE and FCI mean overall mass efficiency, overall carbon efficiency and overall fossil $CO_2$ intensity, respectively, as defined above.

In conclusion, the above calculations confirm that surprisingly the acrylic acid production process of the present invention, which starts from C3-oxygenates which have a favourable $H/C_{eff}$ and which may be obtained from a sugar source (e.g. glucose) which is a renewable feedstock, has a higher route efficiency, in terms of a combination of a higher overall mass efficiency, a higher overall carbon efficiency and a lower overall fossil $CO_2$ intensity, when compared to routes that proceed via propene obtained from glucose as a renewable feedstock. Therefore, advantageously, in addition to valorizing C3-oxygenates formed as undesired (by)products in certain production processes, such as biomass conversion processes, by transforming them into acrylic acid, by means of the present integrated process for the production of acrylic acid, surprisingly, also a high route efficiency is coupled to the use of renewable feedstocks.

Preferably, in the present invention, the C3-oxygenates, originate from converting a renewable feedstock into such C3-oxygenates.

In the present invention, the C3-oxygenates, may originate from converting sugar sources, a renewable feedstock, such as sucrose, glucose, xylose or fructose, into such C3-oxygenates, for example by means of hydrogenolysis or hydrocracking of such sugar sources. These sugars may be used alone or in admixture. Further, these sugars may be present in monomeric, dimeric or polymeric form. Suitable polymeric sugars are cellulose, starch, inulin and hemicellulose.

In the present process wherein acrylic acid is produced and wherein acrolein is an intermediate that is converted into acrylic acid, the acrolein may be obtained from the C3-oxygenate in a variety of ways. In FIG. 1, a number of preparation routes starting from C3-oxygenates and resulting in acrolein are shown.

For a list of C3-oxygenates which may suitably be used in the present process wherein acrolein is an intermediate, reference is made to the above lists of C3-oxygenates containing 1, 2 or 3 oxygen atoms. Preferably, the C3-oxygenate contains 1 or 2 oxygen atoms, such as the C3-oxygenates as shown in FIG. 1 (excluding acrolein and glycerol). More preferably, the C3-oxygenate contains 2 oxygen atoms.

Preferably, in the present process, the C3-oxygenate is a C3-hydroxycarbonyl, in which case the process comprises:
converting the C3-hydroxycarbonyl into acrolein; and
converting the acrolein into acrylic acid.

Said C3-hydroxycarbonyl contains 3 carbon atoms and 2 oxygen atoms in the form of a hydroxyl group and a carbonyl group. The other atoms in such C3-diol and C3-hydroxycarbonyl are hydrogen atoms. In the present process, said C3-hydroxycarbonyl may be monohydroxyacetone, 2-hydroxypropanal or 3-hydroxypropanal. Preferably, said C3-hydroxycarbonyl is a mixture of monohydroxyacetone and 2-hydroxypropanal.

Further, in the present process, the C3-oxygenate may be a C3-hydroxycarbonyl, preferably a mixture of monohydroxyacetone and 2-hydroxypropanal, in which case the process comprises:
converting the C3-hydroxycarbonyl into acrolein; and
converting the acrolein into acrylic acid.

One C3-hydroxycarbonyl or a mixture of two or more different C3-hydroxycarbonyls may be used in the present process. In a case where two or more different C3-hydroxycarbonyls are used, preferably, a mixture of 2-hydroxypropanal and 3-hydroxypropanal is used. Said C3-hydroxycarbonyls may advantageously be converted into acrolein in a single dehydration step without prior separation of the C3-hydroxycarbonyls.

Further, in the present process, any mixture of one or more C3-hydroxycarbonyls with one or more C3-diols, such a monopropylene glycol may be used.

Further, in the present process, in addition to the C3-oxygenate being a C3-hydroxycarbonyl optionally in a mixture with monopropylene glycol, glycerol may also be present and be converted into acrolein simultaneously. In such case, glycerol does not need to be removed beforehand but can advantageously be co-processed with the C3-oxygenate to produce acrolein.

The reactions from the preparation routes in FIG. 1 may be carried out in ways as will be exemplified hereinbelow. The ways in which these reactions may be carried out are not essential to obtaining the above-discussed advantages of the present invention.

In FIG. 1, the designation "—$H_2$" refers to dehydrogenation in general. Such dehydrogenation may be either an endothermic dehydrogenation or an exothermic oxidative dehydrogenation wherein oxygen is added and water is released or a hydrogen transfer reaction. Therefore, in FIG. 1, the designation "—$H_2$" also covers "+0.5$O_2$/—$H_2O$" (i.e. exothermic oxidative dehydrogenation) and hydrogen transfer, according to which $H_2$ is not released as $H_2$ or $H_2O$ but as hydrogenated product such as alcohol (from a ketone) or alkane (from an olefin).

In general, there are the following types of reactions:
(1) reactions involving hydrogenation of a carbonyl group to a hydroxyl group;
(2) reactions involving dehydrogenation of a hydroxyl group to a carbonyl group or dehydrogenation of a carbonyl group to an α,β-unsaturated carbonyl group;
(3) reactions involving oxidation of an aldehyde group or a primary hydroxyl group to a carboxylic acid group;
(4) reactions involving dehydration of alcohols optionally followed by keto-enol rearrangement (e.g. monopropylene glycol to propanal or glycerol to 3-hydroxypropanal) or by hydrogenation of the resulting double carbon-carbon bond (glycerol to monopropylene glycol); and
(5) reactions involving hydroxyl-carbonyl isomerisation.

Reactions involving hydrogenation of a carbonyl group to a hydroxyl group as mentioned above under (1), may be carried out at a relatively low temperature, for example below 200° C., and a relatively high hydrogen pressure, for example higher than 10 bar. The catalyst may be a supported metal catalyst.

Reactions involving dehydrogenation of a hydroxyl group to a carbonyl group or dehydrogenation of a carbonyl group to an α,β-unsaturated carbonyl group as mentioned above under (2), may be carried out at a relatively high temperature, for example above 200° C., and a relatively low hydrogen pressure, for example lower than 1 bar. The catalyst may be a supported metal catalyst.

Reactions involving oxidation of an aldehyde group or a primary hydroxyl group to a carboxylic acid group as mentioned above under (3), may be carried out in the liquid phase at a relatively low temperature, for example at or below 200° C., in the presence of a base and an oxygen containing gas. The catalyst may be a supported metal catalyst, wherein the metal may be a noble metal, such as gold. Alternatively, it may be carried out in the gas phase at a relatively high temperature, for example of from 250 to 350° C., in the presence of an oxygen containing gas. The catalyst may be a mixed oxide that may be partly reduced under the reaction conditions.

Reactions involving dehydration of alcohols as mentioned above under (4), may be carried out in the gas phase at a relatively high temperature, for example at or above 150° C., suitably of from 150 to 400° C., using a solid acid and/or base catalyst. A keto-enol rearrangement may occur spontaneously over such catalysts. For a hydrogenation of the double carbon-carbon bond, the acid/base catalyst may also contain some hydrogenation activity. Such hydrogenation reaction may be carried out at a relatively high hydrogen pressure, for example higher than 10 bar.

Reactions involving hydroxyl-carbonyl isomerisation as mentioned above under (6), may be carried out using any catalyst at a relatively low temperature, for example higher than 100° C., and may even be carried in the absence of a catalyst at an elevated temperature.

That which is claimed is:

1. A process for producing acrylic acid, comprising:
   converting a C3-oxygenate into acrolein, wherein said C3-oxygenate is a compound which contains 3 carbon atoms and 1, 2 or 3 oxygen atoms and wherein said C3-oxygenate is selected from the group consisting of 1-propanol, monohydroxyacetone, 2-hydroxypropanal, dihydroxyacetone and 2,3-dihydroxypropanal; and
   converting the acrolein into acrylic acid, wherein the C3-oxygenate originates from converting a renewable feedstock into the C3-oxygenate.

2. A process according to claim 1, wherein the C3-oxygenate is monohydroxyacetone or 2-hydroxypropanal.

3. A process according to claim 1, wherein the renewable feedstock is a sugar source.

4. A process according to claim 1, wherein the C3-oxygenate is a
   mixture of monohydroxyacetone and 2-hydroxypropanal.

\* \* \* \* \*